United States Patent
Adler et al.

(10) Patent No.: US 11,529,050 B2
(45) Date of Patent: *Dec. 20, 2022

(54) SYSTEMS AND METHODS FOR DETERMINING CROSS-LINKING DISTRIBUTION IN A CORNEA AND/OR STRUCTURAL CHARACTERISTICS OF A CORNEA

(71) Applicant: Avedro, Inc., Waltham, MA (US)

(72) Inventors: Desmond Christopher Adler, Bedford, MA (US); Jun Zhang, Lexington, MA (US); Mikhail Z. Smirnov, North Andover, MA (US); Marc D. Friedman, Needham, MA (US); David Usher, Waltham, MA (US); Grace Elizabeth Lytle, Boston, MA (US); David C. Iannetta, Cambridge, MA (US)

(73) Assignee: AVEDRO, INC., Waltham, MA (US)

( * ) Notice: Subject to any disclaimer, the term of this patent is extended or adjusted under 35 U.S.C. 154(b) by 235 days.

This patent is subject to a terminal disclaimer.

(21) Appl. No.: 16/840,317

(22) Filed: Apr. 3, 2020

(65) Prior Publication Data

US 2020/0229692 A1 Jul. 23, 2020

Related U.S. Application Data

(63) Continuation of application No. 15/868,457, filed on Jan. 11, 2018, now Pat. No. 10,631,726.
(Continued)

(51) Int. Cl.
*A61B 3/107* (2006.01)
*A61F 9/007* (2006.01)
(Continued)

(52) U.S. Cl.
CPC .............. *A61B 3/107* (2013.01); *A61B 3/10* (2013.01); *A61B 3/14* (2013.01); *A61B 5/0036* (2018.08);
(Continued)

(58) Field of Classification Search
CPC .. A61B 3/107; A61B 3/10; A61B 3/14; A61B 5/0036; A61B 5/0071;
(Continued)

(56) References Cited

U.S. PATENT DOCUMENTS

| 5,450,144 A | 9/1995 | Ben Nun |
| 5,512,966 A | 4/1996 | Snook |

(Continued)

FOREIGN PATENT DOCUMENTS

| WO | 2007053826 A2 | 11/2007 |
| WO | 2007139927 A1 | 12/2007 |

(Continued)

OTHER PUBLICATIONS

Li, C. et al. "Elastic Properties of Soft Tissue-Mimicking Phantoms Assessed by Combined Use of Laser Ultrasonics and Low Coherence Interferometry." Optics Express. vol. 19, No. 11, May 9, 2011 (pp. 10153-10163).
(Continued)

*Primary Examiner* — Mohammed A Hasan
(74) *Attorney, Agent, or Firm* — K&L Gates LLP

(57) ABSTRACT

In a corneal measurement system, an optical element focuses an excitation light to an area of corneal tissue at a selected depth. In response, a fluorescing agent applied to the cornea generates a fluorescence emission. An aperture of a pinhole structure selectively transmits the fluorescence emission from the area of corneal tissue at the selected depth. A detector captures the selected fluorescence emission transmitted by the aperture and communicates information relat- (Continued)

ing to a measurement of the selected fluorescence emission captured by the detector. A controller receives the information from the detector and determines a measurement of the fluorescing agent in the area of corneal tissue at the selected depth. The system may include a scan mechanism that causes the optical element to scan the cornea at a plurality of depths, and the controller may determine a measurement of the fluorescing agent in the cornea as a function of depth.

20 Claims, 9 Drawing Sheets

Related U.S. Application Data

(60) Provisional application No. 62/573,440, filed on Oct. 17, 2017, provisional application No. 62/444,910, filed on Jan. 11, 2017.

(51) Int. Cl.
*A61B 3/14* (2006.01)
*A61N 5/06* (2006.01)
*A61B 3/10* (2006.01)
*A61B 5/00* (2006.01)
*A61F 9/008* (2006.01)

(52) U.S. Cl.
CPC ............ *A61F 9/0079* (2013.01); *A61N 5/062* (2013.01); *A61B 5/0071* (2013.01); *A61B 5/4848* (2013.01); *A61F 2009/00872* (2013.01); *A61N 2005/0661* (2013.01)

(58) Field of Classification Search
CPC ... A61B 5/4848; A61B 3/1025; A61B 5/4836; A61F 9/0079; A61F 2009/00872; A61N 5/062; A61N 2005/0661
USPC ........................................................ 351/221
See application file for complete search history.

(56) References Cited

U.S. PATENT DOCUMENTS

| | | | |
|---|---|---|---|
| 5,562,656 A | 10/1996 | Sumiya | |
| 5,608,472 A | 3/1997 | Szirth et al. | |
| 5,786,893 A | 7/1998 | Fink et al. | |
| 5,891,131 A | 4/1999 | Rajan et al. | |
| 6,270,221 B1 | 8/2001 | Liang et al. | |
| 6,319,273 B1 | 11/2001 | Chen et al. | |
| 6,520,958 B1 | 2/2003 | Shimmick et al. | |
| 6,571,118 B1 | 5/2003 | Utzinger et al. | |
| 7,004,902 B2 | 2/2006 | Luce | |
| 7,871,378 B1 | 1/2011 | Chou et al. | |
| 7,889,348 B2 * | 2/2011 | Tearney | A61B 1/07 356/451 |
| 8,115,919 B2 | 2/2012 | Yun et al. | |
| 10,631,726 B2 * | 4/2020 | Adler | A61B 3/14 |
| 2001/0055095 A1 | 12/2001 | D'Souza et al. | |
| 2003/0135122 A1 | 7/2003 | Bambot et al. | |
| 2003/0189689 A1 | 10/2003 | Rathjen | |
| 2003/0231285 A1 | 12/2003 | Ferguson | |
| 2004/0199079 A1 | 10/2004 | Chuck et al. | |
| 2005/0096515 A1 | 5/2005 | Geng | |
| 2006/0033933 A1 * | 2/2006 | Feierabend | G01N 21/6458 356/512 |
| 2006/0058592 A1 | 3/2006 | Bouma et al. | |
| 2006/0106371 A1 | 5/2006 | Muhlhoff et al. | |
| 2007/0291277 A1 | 12/2007 | Everett et al. | |
| 2009/0116096 A1 | 5/2009 | Zalevsky et al. | |
| 2009/0271155 A1 | 10/2009 | Dupps, Jr. et al. | |
| 2009/0275929 A1 | 11/2009 | Zickler | |
| 2010/0149487 A1 | 6/2010 | Ribak | |
| 2010/0204584 A1 | 8/2010 | Ornberg et al. | |
| 2011/0118654 A1 | 5/2011 | Muller et al. | |
| 2011/0237999 A1 * | 9/2011 | Muller | A61N 5/0625 351/215 |
| 2011/0264082 A1 | 10/2011 | Mrochen et al. | |
| 2011/0288466 A1 | 11/2011 | Muller et al. | |
| 2012/0083772 A1 | 4/2012 | Rubinfeld et al. | |
| 2012/0215155 A1 | 8/2012 | Muller et al. | |
| 2012/0283621 A1 | 11/2012 | Muller | |
| 2012/0289886 A1 | 11/2012 | Muller et al. | |
| 2012/0303008 A1 | 11/2012 | Muller et al. | |
| 2012/0310083 A1 | 12/2012 | Friedman et al. | |
| 2013/0060187 A1 | 3/2013 | Friedman et al. | |
| 2013/0085370 A1 | 4/2013 | Friedman et al. | |
| 2014/0368792 A1 * | 12/2014 | Friedman | A61B 3/14 351/212 |
| 2014/0368793 A1 | 12/2014 | Friedman et al. | |
| 2015/0018674 A1 * | 1/2015 | Scott | A61B 5/0073 600/407 |
| 2016/0310319 A1 | 10/2016 | Kamaev et al. | |
| 2016/0338588 A1 | 11/2016 | Friedman | |

FOREIGN PATENT DOCUMENTS

| | | |
|---|---|---|
| WO | 2007143111 A2 | 12/2007 |
| WO | 2008095075 A1 | 8/2008 |
| WO | 2012149570 A1 | 11/2012 |
| WO | 2012174453 A2 | 12/2012 |
| WO | 2014202736 A1 | 12/2014 |

OTHER PUBLICATIONS

Li, C. et al. "Noncontact All-Optical Measurement of Corneal Elasticity." Optics Letters. vol. 37, No. 10, May 15, 2012 (pp. 1625-1627).

Li, P. et al. "In Vivo Microstructural and Microvascular Imaging of the Human Corneo-Scleral Limbus Using Optical Coherence Tomography." Biomedical Optics Express. vol. 2, No. 11, Oct. 18, 2011 (pp. 3109-3118).

Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238 (8 pages).

Fite et al. Noninvasive Multimodal Evaluation of Bioengineered Cartilage Constructs Combining Time-Resolved Fluorescence and Ultrasound Imaging. Tissue Eng: Part C vol. 17, No. 4, 2011 (10 pages).

Hitzenberger et al., "Birefringence Properties of the Human Cornea Measured With Polarization Sensitive Optical Coherence Tomography," Bull. Soc. Beige Ophtalmol., 302, 153-168, 2006 (16 pages).

Rolandi et al. Correlation of Collagen-Linked Fluorescence and Tendon Fiber Breaking Time. Gerontology 1991;27:240-243 (4 pages).

Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," J. Cataract Refract. Surgery, vol. 35, No. 6, pp. 1055-1062; Jun. 2009 (8 pages).

Friedman, M. et al. "Advanced Corneal Cross-Linking System with Fluorescence Dosimetry", Journal of Ophthalmology, vol. 2012, Article ID 303459, dated May 7, 2012 (6 pages).

Randall, J. et al., "The Measurementand Intrepretation of Brillouin Scattering in the Lens of the Eye," The Royal Society, Abstract only, published 2013 [available online at http://rspb.royalsocietypublishing.org/content/214/1197/449.short] (1 page).

Scarcelli, G. et al., "Brillouin Optical Microscopy for Corneal Biomechanics", Investigative Ophthalmology & Visual Science, Jan. 2012, vol. 53, No. 1, pp. 185-190 (6 pages).

Reiss, S. et al., "Spatially resolved Brillouin Spectroscopy to determine the rheological properties of the eye lens", Biomedical Optics Express, vol. 2, No. 8, p. 2144, Aug. 1, 2011 (16 pages).

Arboleda A, Kowalczuk L, Savoldelli M, et al. Evaluating in vivo delivery of riboflavin with coulomb-controlled iontophoresis for

(56) References Cited

OTHER PUBLICATIONS corneal collagen cross-linking: a pilot study. Invest Ophthalmol Vis Sci. 2014;55:2731-2738 (8 pages).
International Search Report issued in co-pending International Patent Application No. PCT/US2018/013311, ISA/RU, dated May 24, 2018, 2 pages.
Written Opinion of the International Searching Authority issued in co-pending International Patent Application No. PCT/US2018/013311, ISA/RU, dated May 24, 2018, 4 pages.

\* cited by examiner

SYSTEMS AND METHODS FOR DETERMINING CROSS-LINKING DISTRIBUTION IN A CORNEA AND/OR STRUCTURAL CHARACTERISTICS OF A CORNEA

CROSS-REFERENCE TO RELATED APPLICATIONS

This application is a continuation application of U.S. patent application Ser. No. 15/868,457, filed Jan. 11, 2018, which claims the benefit of, and priority to, U.S. Provisional Patent Application Ser. No. 62/444,910, filed on Jan. 11, 2017, and U.S. Provisional Patent Application Ser. No. 62/573,440, filed on Oct. 17, 2017, the contents of these applications being incorporated entirely herein by reference.

BACKGROUND

Field

The present disclosure pertains to systems and methods for eye treatments or procedures, and more particularly, to systems and methods that determine a distribution of a cross-linking agent in a cornea and/or to determine structural characteristics of a cornea, e.g., corneal thickness.

Description of Related Art

Cross-linking treatments may be employed to treat eyes suffering from disorders, such as keratoconus. In particular, keratoconus is a degenerative disorder of the eye in which structural changes within the cornea cause it to weaken and change to an abnormal conical shape. Cross-linking treatments can strengthen and stabilize areas weakened by keratoconus and prevent undesired shape changes.

Cross-linking treatments may also be employed after surgical procedures, such as Laser-Assisted in situ Keratomileusis (LASIK) surgery. For instance, a complication known as post-LASIK ectasia may occur due to the thinning and weakening of the cornea caused by LASIK surgery. In post-LASIK ectasia, the cornea experiences progressive steepening (bulging). Accordingly, cross-linking treatments can strengthen and stabilize the structure of the cornea after LASIK surgery and prevent post-LASIK ectasia.

Cross-linking treatments may also be employed to induce refractive changes in the cornea to correct disorders such as myopia, hyperopia, myopia, hyperopia, astigmatism, irregular astigmatism, presbyopia, etc.

SUMMARY

According to aspects of the present disclosure, systems and methods employ illumination and imaging techniques to determine a distribution of a cross-linking agent in a cornea. Additionally or alternatively, systems and methods employ illumination and imaging techniques to determine structural characteristics of a cornea, such as corneal thickness.

According to one embodiment, a measurement system for a cornea includes a light source configured to emit an excitation light that causes a fluorescing agent, e.g., a cross-linking agent, applied to a cornea to generate a fluorescence emission. The system includes an optical element positioned to receive the excitation light from the light source and configured to focus the excitation light to an area of corneal tissue at a selected depth of the cornea. The fluorescing agent in the cornea generates the fluorescence emission in response to the excitation light. The system includes a pinhole structure including an aperture. The pinhole structure is positioned to receive the fluorescence emission from the fluorescing agent in the cornea. The aperture is configured to selectively transmit the fluorescence emission from the area of corneal tissue at the selected depth. The system includes a detector positioned to capture the selected fluorescence emission transmitted by the aperture and to communicate information relating to a measurement of the selected fluorescence emission captured by the detector. The system includes a controller communicatively coupled to the detector and configured to receive the information from the detector and to determine, based on the information, a measurement of the fluorescing agent in the area of corneal tissue at the selected depth.

In some cases, the measurement system may include a scan mechanism configured to cause the optical element to scan the cornea at a plurality of depths and to focus the excitation light on a respective area of corneal tissue at each depth. For each depth: (i) the aperture of the pinhole structure is configured to selectively transmit the fluorescence emission from the respective area of corneal tissue, and (ii) the detector is configured to capture the selected fluorescence emission transmitted by the aperture and configured to communicate information relating to a measurement of the selected fluorescence emission captured by the detector. The controller is configured to receive the information from the detector for each depth and to determine, based on the information for the plurality of depths, a measurement of the fluorescing agent in the cornea as a function of depth. The plurality of depths may extend from an anterior surface of the cornea to a posterior surface of the cornea, and the controller may be further configured to determine, based on the information for the plurality of depths, at least one of a location of the posterior surface, a distance between the anterior surface and the posterior surface, or a location of an interface between sections of the cornea.

According to another embodiment, a measurement system for a cornea includes a light source configured to emit an incidence light. The system includes an optical element positioned to receive the incidence light from the light source and configured to focus the incidence light to an area of corneal tissue at a selected depth of the cornea. The area of corneal tissue reflects the incidence light. The system includes a scan mechanism configured to cause the optical element to scan the cornea at a plurality of depths and to focus the excitation light on a respective area of corneal tissue at each depth. The plurality of depths extending from an anterior surface of the cornea to a posterior surface of the cornea. The system includes a pinhole structure including an aperture. The pinhole structure is positioned to receive, for each depth, the reflected light from the respective area of corneal tissue. The aperture is configured, for each depth, to selectively transmit the reflected light from the respective area of corneal tissue. The system includes a detector positioned to capture the selected reflected light transmitted by the aperture for each depth and configured to communicate, for each depth, information relating to a measurement of the selected reflected light captured by the detector. The system includes a controller communicatively coupled to the detector and configured to receive the information from the detector for each depth and to determine, based on the information for the plurality of depths, at least one of a location of the posterior surface, a distance between the anterior surface and the posterior surface, or a location of a sub-corneal interface.

According to yet another embodiment, a measurement system for a cornea, includes a light source configured to emit an excitation light that causes a fluorescing agent applied to a cornea to generate a fluorescence emission. The system includes at least one optical element positioned to receive the excitation light from the light source and configured to deliver the excitation light. The excitation light extends through a plurality of depths of the cornea. The fluorescing agent in the cornea generates the fluorescence emission in response to the excitation light. The system includes a detector positioned to capture an image of the fluorescence emission from the cornea. The system includes a controller communicatively coupled to the detector and configured to: receive the image from the detector, scan the image to measure the fluorescence emission at the plurality of depths, and to determine a measurement of the fluorescing agent in the cornea as a function of depth based on the measurement of the fluorescence emission at the plurality of depths. The excitation light may further extend in at least one lateral direction as it extends through the plurality of depths of the cornea, and the controller may be further configured to scan the image to measure the fluorescence emission along the at least one lateral direction at the plurality of depths, and to determine a measurement of the fluorescing agent in the cornea as a function of depth and lateral location based on the measurement of the fluorescence emission along the at least one transverse direction at the plurality of depths.

Figure 1:
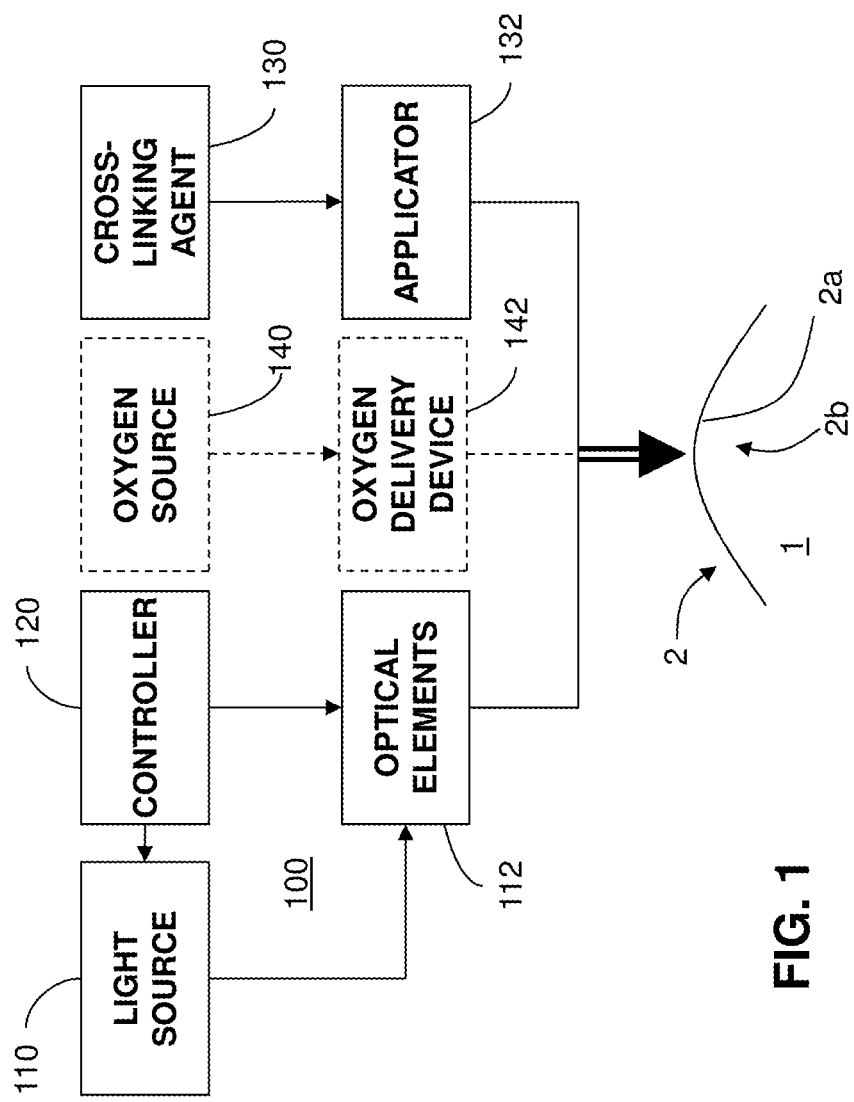
FIG. 1 illustrates an example system that delivers a cross-linking agent and photoactivating light to a cornea of an eye in order to generate cross-linking of corneal collagen, according to aspects of the present disclosure.

While the present disclosure is susceptible to various modifications and alternative forms, a specific embodiment thereof has been shown by way of example in the drawings and will herein be described in detail. It should be understood, however, that it is not intended to limit the present disclosure to the particular forms disclosed, but on the contrary, the intention is to cover all modifications, equivalents, and alternatives falling within the spirit of the present disclosure.

DESCRIPTION

FIG. 1 illustrates an example treatment system 100 for generating cross-linking of collagen in a cornea 2 of an eye 1. The treatment system 100 includes an applicator 132 for applying a cross-linking agent 130 to the cornea 2. In example embodiments, the applicator 132 may be an eye dropper, syringe, or the like that applies the photosensitizer 130 as drops to the cornea 2. Example systems and methods for applying the cross-linking agent is described in U.S. patent application Ser. No. 15/486,778, filed Apr. 13, 2017 and titled "Systems and Methods for Delivering Drugs to an Eye," the contents of which are incorporated entirely herein by reference.

The cross-linking agent 130 may be provided in a formulation that allows the cross-linking agent 130 to pass through the corneal epithelium 2a and to underlying regions in the corneal stroma 2b. Alternatively, the corneal epithelium 2a may be removed or otherwise incised to allow the cross-linking agent 130 to be applied more directly to the underlying tissue.

The treatment system 100 includes an illumination system with a light source 110 and optical elements 112 for directing light to the cornea 2. The light causes photoactivation of the cross-linking agent 130 to generate cross-linking activity in the cornea 2. For example, the cross-linking agent may include riboflavin and the photoactivating light may include ultraviolet A (UVA) (e.g., approximately 365 nm) light. Alternatively, the photoactivating light may include another wavelength, such as a visible wavelength (e.g., approximately 452 nm). As described further below, corneal cross-linking improves corneal strength by creating chemical bonds within the corneal tissue according to a system of photochemical kinetic reactions. For instance, riboflavin and the photoactivating light may be applied to stabilize and/or strengthen corneal tissue to address diseases such as keratoconus or post-LASIK ectasia.

The treatment system 100 includes one or more controllers 120 that control aspects of the system 100, including the light source 110 and/or the optical elements 112. In an implementation, the cornea 2 can be more broadly treated with the cross-linking agent 130 (e.g., with an eye dropper, syringe, etc.), and the photoactivating light from the light source 110 can be selectively directed to regions of the treated cornea 2 according to a particular pattern.

The optical elements 112 may include one or more mirrors or lenses for directing and focusing the photoactivating light emitted by the light source 110 to a particular pattern on the cornea 2. The optical elements 112 may further include filters for partially blocking wavelengths of light emitted by the light source 110 and for selecting particular wavelengths of light to be directed to the cornea 2 for photoactivating the cross-linking agent 130. In addition, the optical elements 112 may include one or more beam splitters for dividing a beam of light emitted by the light source 110, and may include one or more heat sinks for absorbing light emitted by the light source 110. The optical elements 112 may also accurately and precisely focus the photoactivating light to particular focal planes within the cornea 2, e.g., at a particular depths in the underlying region 2b where cross-linking activity is desired.

Moreover, specific regimes of the photoactivating light can be modulated to achieve a desired degree of cross-linking in the selected regions of the cornea 2. The one or more controllers 120 may be used to control the operation of the light source 110 and/or the optical elements 112 to precisely deliver the photoactivating light according to any combination of: wavelength, bandwidth, intensity, power, location, depth of penetration, and/or duration of treatment (the duration of the exposure cycle, the dark cycle, and the ratio of the exposure cycle to the dark cycle duration).

The parameters for photoactivation of the cross-linking agent 130 can be adjusted, for example, to reduce the amount of time required to achieve the desired cross-linking. In an example implementation, the time can be reduced from minutes to seconds. While some configurations may apply the photoactivating light at an irradiance of 5 mW/cm$^2$, larger irradiance of the photoactivating light, e.g., multiples of 5 mW/cm$^2$, can be applied to reduce the time required to achieve the desired cross-linking. The total dose of energy absorbed in the cornea 2 can be described as an effective dose, which is an amount of energy absorbed through an area of the corneal epithelium 2a. For example the effective dose for a region of the corneal surface 2A can be, for example, 5 J/cm$^2$, or as high as 20 J/cm$^2$ or 30 J/cm$^2$. The effective dose described can be delivered from a single application of energy, or from repeated applications of energy.

The optical elements 112 of the treatment system 100 may include a digital micro-mirror device (DMD) to modulate the application of photoactivating light spatially and temporally. Using DMD technology, the photoactivating light from the light source 110 is projected in a precise spatial pattern that is created by microscopically small mirrors laid out in a matrix on a semiconductor chip. Each mirror represents one or more pixels in the pattern of projected light. With the DMD one can perform topography guided cross-linking. The control of the DMD according to topography may employ several different spatial and temporal irradiance and dose profiles. These spatial and temporal dose profiles may be created using continuous wave illumination but may also be modulated via pulsed illumination by pulsing the illumination source under varying frequency and duty cycle regimes. Alternatively, the DMD can modulate different frequencies and duty cycles on a pixel by pixel basis to give ultimate flexibility using continuous wave illumination. Or alternatively, both pulsed illumination and modulated DMD frequency and duty cycle combinations may be combined. This allows for specific amounts of spatially determined corneal cross-linking. This spatially determined cross-linking may be combined with dosimetry, interferometry, optical coherence tomography (OCT), corneal topography, etc., for pre-treatment planning and/or real-time monitoring and modulation of corneal cross-linking during treatment. Aspects of a dosimetry system are described in further detail below. Additionally, pre-clinical patient information may be combined with finite element biomechanical computer modeling to create patient specific pre-treatment plans.

To control aspects of the delivery of the photoactivating light, embodiments may also employ aspects of multiphoton excitation microscopy. In particular, rather than delivering a single photon of a particular wavelength to the cornea 2, the treatment system 100 may deliver multiple photons of longer wavelengths, i.e., lower energy, that combine to initiate the cross-linking. Advantageously, longer wavelengths are scattered within the cornea 2 to a lesser degree than shorter wavelengths, which allows longer wavelengths of light to penetrate the cornea 2 more efficiently than light of shorter wavelengths. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules in the cross-linking agent 130 to generate the photochemical kinetic reactions described further below. When a cross-linking agent molecule simultaneously absorbs both photons, it absorbs enough energy to release reactive radicals in the corneal tissue. Embodiments may also utilize lower energy photons such that a cross-linking agent molecule must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

A large number of conditions and parameters affect the cross-linking of corneal collagen with the cross-linking agent 130. For example, the irradiance and the dose of photoactivating light affect the amount and the rate of cross-linking.

When the cross-linking agent 130 is riboflavin in particular, the UVA light may be applied continuously (continuous wave (CW)) or as pulsed light, and this selection has an effect on the amount, the rate, and the extent of cross-linking. If the UVA light is applied as pulsed light, the duration of the exposure cycle, the dark cycle, and the ratio of the exposure cycle to the dark cycle duration have an effect on the resulting corneal stiffening. Pulsed light illumination can be used to create greater or lesser stiffening of corneal tissue than may be achieved with continuous wave illumination for the same amount or dose of energy delivered. Light pulses of suitable length and frequency may be used to achieve more optimal chemical amplification. For pulsed light treatment, the on/off duty cycle may be between approximately $100/1$ to approximately $1/1000$; the irradiance may be between approximately 1 mW/cm$^2$ to approximately 1000 mW/cm$^2$ average irradiance, and the pulse rate may be between approximately 0.01 HZ to approximately 1000 Hz or between approximately 1000 Hz to approximately 100,000 Hz.

The treatment system 100 may generate pulsed light by employing a DMD, electronically turning the light source 110 on and off, and/or using a mechanical or opto-electronic (e.g., Pockels cells) shutter or mechanical chopper or rotating aperture. Because of the pixel specific modulation capabilities of the DMD and the subsequent stiffness impartment based on the modulated frequency, duty cycle, irradiance and dose delivered to the cornea, complex biomechanical stiffness patterns may be imparted to the cornea to allow for various amounts of refractive correction. These refractive corrections, for instance, may involve combinations of myopia, hyperopia, astigmatism, irregular astigmatism, presbyopia and complex corneal refractive surface corrections because of ophthalmic conditions such as keratoconus, pellucid marginal disease, post-LASIK ectasia, and other conditions of corneal biomechanical alteration/degeneration, etc. A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz.

Although example embodiments may employ stepwise on/off pulsed light functions, it is understood that other functions for applying light to the cornea may be employed to achieve similar effects. For example, light may be applied to the cornea according to a sinusoidal function, sawtooth function, or other complex functions or curves, or any combination of functions or curves. Indeed, it is understood that the function may be substantially stepwise where there may be more gradual transitions between on/off values. In addition, it is understood that irradiance does not have to decrease down to a value of zero during the off cycle, and may be above zero during the off cycle. Desired effects may be achieved by applying light to the cornea according to a curve varying irradiance between two or more values.

Examples of systems and methods for delivering photoactivating light are described, for example, in U.S. Patent Application Publication No. 2011/0237999, filed Mar. 18, 2011 and titled "Systems and Methods for Applying and Monitoring Eye Therapy," U.S. Patent Application Publication No. 2012/0215155, filed Apr. 3, 2012 and titled "Systems and Methods for Applying and Monitoring Eye Therapy," and U.S. Patent Application Publication No. 2013/0245536, filed Mar. 15, 2013 and titled "Systems and Methods for Corneal Cross-Linking with Pulsed Light," the contents of these applications being incorporated entirely herein by reference.

The addition of oxygen also affects the amount of corneal stiffening. In human tissue, $O_2$ content is very low compared to the atmosphere. The rate of cross-linking in the cornea, however, is related to the concentration of $O_2$ when it is irradiated with photoactivating light. Therefore, it may be advantageous to increase or decrease the concentration of $O_2$ actively during irradiation to control the rate of cross-linking until a desired amount of cross-linking is achieved. Oxygen may be applied during the cross-linking treatments in a number of different ways. One approach involves supersaturating the riboflavin with $O_2$. Thus, when the riboflavin is applied to the eye, a higher concentration of $O_2$ is delivered directly into the cornea with the riboflavin and affects the reactions involving $O_2$ when the riboflavin is exposed to the photoactivating light. According to another approach, a steady state of $O_2$ (at a selected concentration) may be maintained at the surface of the cornea to expose the cornea to a selected amount of $O_2$ and cause $O_2$ to enter the cornea. As shown in FIG. 1, for instance, the treatment system 100 also includes an oxygen source 140 and an oxygen delivery device 142 that optionally delivers oxygen at a selected concentration to the cornea 2. Example systems and methods for applying oxygen during cross-linking treatments are described, for example, in U.S. Pat. No. 8,574,277, filed Oct. 21, 2010 and titled "Eye Therapy," U.S. Patent Application Publication No. 2013/0060187, filed Oct. 31, 2012 and titled "Systems and Methods for Corneal Cross-Linking with Pulsed Light," the contents of these applications being incorporated entirely herein by reference. Additionally, an example mask device for delivering concentrations of oxygen as well as photoactivating light in eye treatments is described in U.S. Provisional Patent Application Publication No. 2017/0156926, filed Dec. 3, 2016 and titled "Systems and Methods for Treating an Eye with a Mask Device," the contents of which are incorporated entirely herein by reference. For instance, a mask may be placed over the eye(s) to produce a consistent and known oxygen concentration above the surface.

When riboflavin absorbs radiant energy, especially light, it undergoes photoactivation. There are two photochemical kinetic pathways for riboflavin photoactivation, Type I and Type II. Some of the reactions involved in both the Type I and Type II mechanisms are as follows:

Common Reactions:

$$Rf \rightarrow Rf_1^*, l; \tag{r1}$$

$$Rf_1^* \rightarrow Rf, \kappa 1; \tag{r2}$$

$$Rf_1^* \rightarrow Rf_3^*, \kappa 2; \tag{r3}$$

Type I reactions:

$$Rf_3^* + DH \rightarrow RfH^\cdot + D^\cdot, \kappa 3; \tag{r4}$$

$$2RfH^\cdot \rightarrow Rf + RfH_2, \kappa 4; \tag{r5}$$

Type II reactions:

$$Rf_3^* + O_2 \rightarrow Rf + O_2^1, \kappa 5; \tag{r6}$$

$$DH + O_2^1 \rightarrow D_{ox}, \kappa 6; \tag{r7}$$

$$D_{ox} + DH \rightarrow D-D, \kappa 7; CXL \tag{r8}$$

In the reactions described herein, Rf represents riboflavin in the ground state. $Rf_1^*$ represents riboflavin in the excited singlet state. $Rf_3^*$ represents riboflavin in a triplet excited state. $Rf^-$ is the reduced radical anion form of riboflavin. $Rfh^\cdot$ is the radical form of riboflavin. $RfH_2$ is the reduced form of riboflavin. DH is the substrate. $DH^{+\cdot}$ is the intermediate radical cation. $D^\cdot$ is the radical. $D_{ox}$ is the oxidized form of the substrate.

Riboflavin is excited into its triplet excited state $Rf_3^*$ as shown in reactions (r1) to (r3). From the triplet excited state $Rf_3^*$, the riboflavin reacts further, generally according to Type I or Type II mechanisms. In the Type I mechanism, the substrate reacts with the excited state riboflavin to generate radicals or radical ions, respectively, by hydrogen atoms or electron transfer. In Type II mechanism, the excited state riboflavin reacts with oxygen to form singlet molecular oxygen. The singlet molecular oxygen then acts on tissue to produce additional cross-linked bonds.

Oxygen concentration in the cornea is modulated by UVA irradiance and temperature and quickly decreases at the beginning of UVA exposure. Utilizing pulsed light of a specific duty cycle, frequency, and irradiance, input from both Type I and Type II photochemical kinetic mechanisms can be employed to achieve a greater amount of photochemical efficiency. Moreover, utilizing pulsed light allows regulating the rate of reactions involving riboflavin. The rate of reactions may either be increased or decreased, as needed, by regulating, one of the parameters such as the irradiance, the dose, the on/off duty cycle, riboflavin concentration, soak time, and others. Moreover, additional ingredients that affect the reaction and cross-linking rates may be added to the cornea.

If UVA radiation is stopped shortly after oxygen depletion, oxygen concentrations start to increase (replenish). Excess oxygen may be detrimental in the corneal cross-linking process because oxygen is able to inhibit free radical photopolymerization reactions by interacting with radical species to form chain-terminating peroxide molecules. The pulse rate, irradiance, dose, and other parameters can be adjusted to achieve a more optimal oxygen regeneration rate. Calculating and adjusting the oxygen regeneration rate is another example of adjusting the reaction parameters to achieve a desired amount of corneal stiffening.

Oxygen content may be depleted throughout the cornea, by various chemical reactions, except for the very thin corneal layer where oxygen diffusion is able to keep up with the kinetics of the reactions. This diffusion-controlled zone will gradually move deeper into the cornea as the reaction ability of the substrate to uptake oxygen decreases.

Riboflavin is reduced (deactivated) reversibly or irreversibly and/or photo-degraded to a greater extent as irradiance increases. Photon optimization can be achieved by allowing reduced riboflavin to return to ground state riboflavin in Type I reactions. The rate of return of reduced riboflavin to ground state in Type I reactions is determined by a number of factors. These factors include, but are not limited to, on/off duty cycle of pulsed light treatment, pulse rate frequency, irradiance, and dose. Moreover, the riboflavin concentration, soak time, and addition of other agents, including oxidizers, affect the rate of oxygen uptake. These and other parameters, including duty cycle, pulse rate frequency, irradiance, and dose can be selected to achieve more optimal photon efficiency and make efficient use of both Type I as well as Type II photochemical kinetic mechanisms for riboflavin photosensitization. Moreover, these parameters can be selected in such a way as to achieve a more optimal chemical amplification effect.

In addition to the photochemical kinetic reactions (r1)-(r8) above, however, the present inventors have identified the following photochemical kinetic reactions (r9)-(r26) that also occur during riboflavin photoactivation:

| | | |
|---|---|---|
| $Rf_3^* \rightarrow Rf$, | $k8$; | (r9) |
| $Rf_3^* + Rf \rightarrow 2RfH^{\cdot}$, | $k9$; | (r10) |
| $RfH_2 + O_2 \rightarrow RfH^{\cdot} + H^+ + O_2^-$, | $k10$; | (r11) |
| $RfH^{\cdot} + O_2 \rightarrow Rf + H^+ + O_2^-$, | $k11$; | (r12) |
| $2\,RfH_2 + O_2^- \rightarrow 2\,RfH^{\cdot} + H_2O_2$, | $k12$; | (r13) |
| $2\,RfH^{\cdot} + O_2^- \rightarrow 2\,Rf + H_2O_2$, | $k13$; | (r14) |
| $RfH^{\cdot} + H_2O_2 \rightarrow OH^{\cdot} + Rf + H_2O$, | $k14$; | (r15) |
| $OH^{\cdot} + DH \rightarrow D^{\cdot} + H_2O$, | $k15$; | (r16) |
| $D^{\cdot} + D^{\cdot} \rightarrow D-D$, | $k16$; CXL | (r17) |
| $O_2^1 \rightarrow O_2$, | $k18$; | (r18) |
| $D^{\cdot} + RfH_2 \rightarrow RfH^{\cdot} + DH$, | $k19$; | (r19) |
| $Rf + Rf \underset{\kappa_a^-}{\overset{\kappa_a^+}{\rightleftharpoons}} A_1$, | $K_a = \kappa_a^+ / \kappa_a^-$ | (r20) |
| $RfH_2 + RfH_2 \underset{\kappa_a^-}{\overset{\kappa_a^+}{\rightleftharpoons}} A_2$, | $K_a = \kappa_a^+ / \kappa_a^-$ | (r21) |
| $Rf + RfH_2 \underset{\kappa_b^-}{\overset{\kappa_b^+}{\rightleftharpoons}} A_3$, | $K_b = \kappa_b^+ / \kappa_b^-$ | (r22) |
| $Rf_1^* + A \rightarrow Rf + A$, | $\kappa_{1a}$ | (r23) |
| $Rf_3^* + A \rightarrow Rf + A$, | $\kappa_{3a}$ | (r24) |
| $2\,O_2^- \rightarrow O_2 + H_2O_2$, | $k12$ | (r25) |
| $OH^{\cdot} + CXL \rightarrow$ inert products, | $\kappa_{OH}$ | (r26) |

Figure 2A:
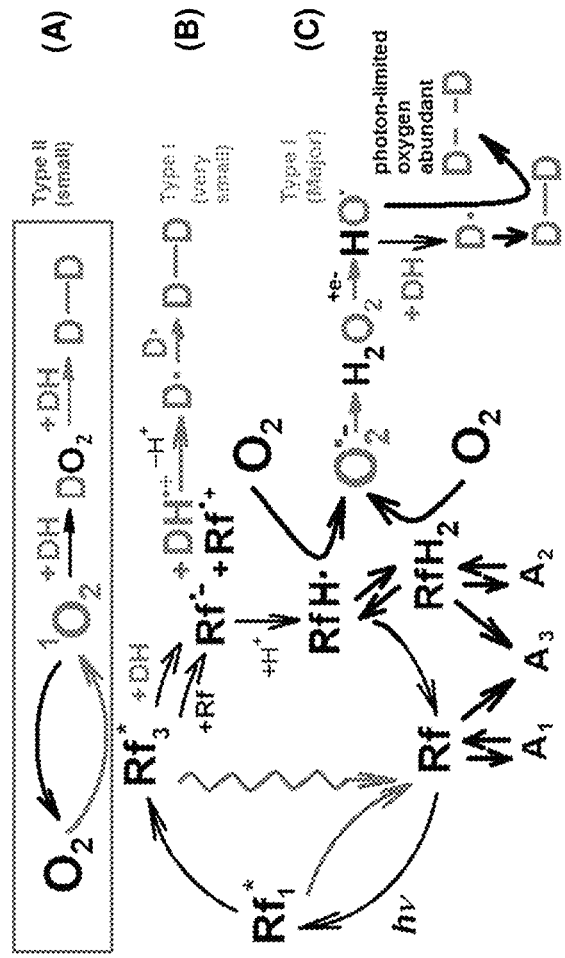
FIG. 2A illustrates a diagram for photochemical kinetic reactions involving riboflavin and photoactivating light (e.g., ultraviolet A (UVA) light) applied during a corneal cross-linking treatment, according to aspects of the present disclosure.

FIG. 2A illustrates a diagram for the photochemical kinetic reactions provided in reactions (r1) through (r26) above. The diagram summarizes photochemical transformations of riboflavin (Rf) under UVA photoactivating light and its interactions with various donors (DH) via electron transfer. As shown, cross-linking activity occurs: (A) through the presence of singlet oxygen in reactions (r6) through (r8) (Type II mechanism); (B) without using oxygen in reactions (r4) and (r17) (Type I mechanism); and (C) through the presence of peroxide ($H_2O_2$), superoxide ($O_2^-$), and hydroxyl radicals ($\cdot OH$) in reactions (r13) through (r17).

As shown in FIG. 2A, the present inventors have also determined that the cross-linking activity is generated to a greater degree from reactions involving peroxide, superoxide, and hydroxyl radicals. Cross-linking activity is generated to a lesser degree from reactions involving singlet oxygen and from non-oxygen reactions. Some models based on the reactions (r1)-(r26) can account for the level of cross-linking activity generated by the respective reactions. For instance, where singlet oxygen plays a smaller role in generating cross-linking activity, models may be simplified by treating the cross-linking activity resulting from singlet oxygen as a constant.

All the reactions start from $Rf_3^*$ as provided in reactions (r1)-(r3). The quenching of $Rf_3^*$ occurs through chemical reaction with ground state Rf in reaction (r10), and through deactivation by the interaction with water in reaction (r9).

As described above, excess oxygen may be detrimental in corneal cross-linking process. As shown in FIG. 2A, when the system becomes photon-limited and oxygen-abundant, cross-links can be broken from further reactions involving superoxide, peroxide, and hydroxyl radicals. Indeed, in some cases, excess oxygen may result in net destruction of cross-links versus generation of cross-links.

As described above, a large variety of factors affect the rate of the cross-linking reaction and the amount of biomechanical stiffness achieved due to cross-linking. A number of these factors are interrelated, such that changing one factor may have an unexpected effect on another factor. However, a more comprehensive model for understanding the relationship between different factors for cross-linking treatment is provided by the photochemical kinetic reactions (r1)-(r26) identified above. Accordingly, systems and methods can adjust various parameters for cross-linking treatment according to this photochemical kinetic cross-linking model, which provides a unified description of oxygen dynamics and cross-linking activity. The model can be employed to evaluate expected outcomes based on different combinations of treatment parameters and to identify the combination of treatment parameters that provides the desired result. The parameters, for example, may include, but are not limited to: the concentration(s) and/or soak times of the applied cross-linking agent; the dose(s), wavelength(s), irradiance(s), duration(s), and/or on/off duty cycle(s) of the photoactivating light; the oxygenation conditions in the tissue; and/or presence of additional agents and solutions.

Figure 2B:
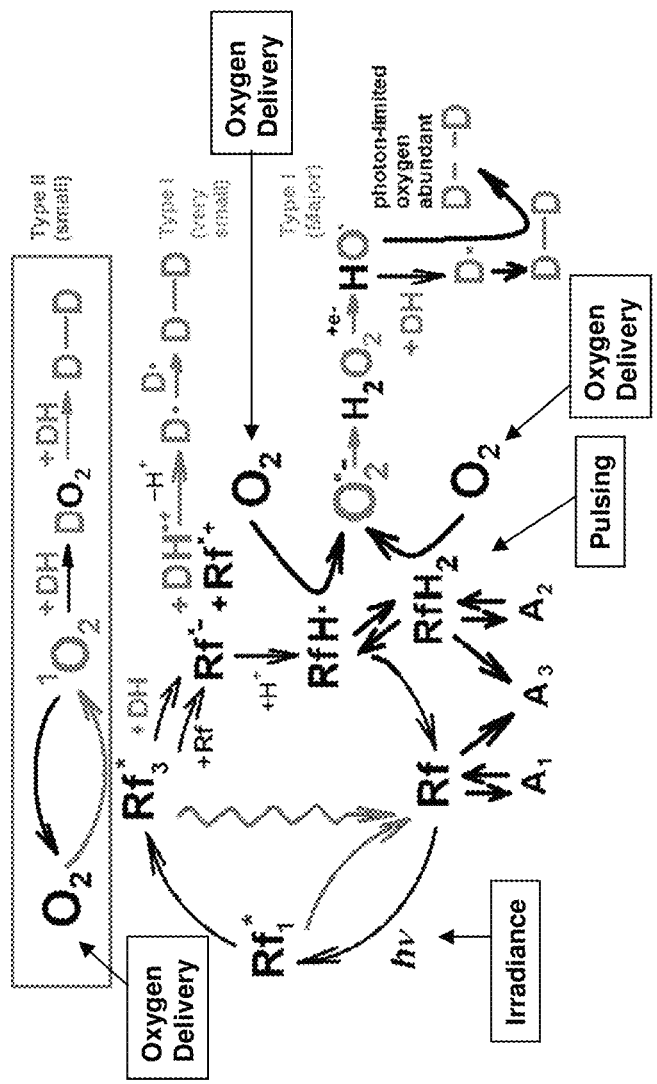
FIG. 2B illustrates a diagram for parameters that can affect the photochemical kinetic reactions shown in FIG. 2A.

As shown in FIG. 2B, aspects of the system of reactions can be affected by different parameters. For instance, the irradiance at which photoactivating light is delivered to the system affects the photons available in the system to generate $Rf_3^*$ for subsequent reactions. Additionally, delivering greater oxygen into the system drives the oxygen-based reactions. Meanwhile, pulsing the photoactivating light affects the ability of the reduced riboflavin to return to ground state riboflavin by allowing additional time for oxygen diffusion. Of course, other parameters can be varied to control the system of reactions.

Further aspects of the photochemical kinetic reactions provided in reactions (r1)-(r26) are described in U.S. Patent Application Publication No. 2016/0310319, filed Apr. 27, 2016 and titled "Systems and Methods for Cross-Linking Treatments of an Eye," the contents of which are incorporated entirely herein by reference.

When light of a particular wavelength is applied to a cross-linking agent, such as riboflavin, the light can excite the cross-linking agent and cause the cross-linking agent to fluoresce. As such, an excitation light can be employed to cause a cross-linking agent in corneal tissue to fluoresce and determine how the cross-linking agent is distributed in the corneal tissue. When an image of the cornea is taken during the application of the excitation light, the intensity (magnitude) of the fluorescence, for instance, can be measured to determine the amount, i.e., dose, of cross-linking agent taken up by the corneal tissue. Using these principles, dosimetry systems can determine the presence and distribution of the cross-linking agent in the cornea by capturing one or more images of the fluorescence from the cross-linking agent as it responds to the excitation light. Aspects of such systems are described, for instance, in U.S. Pat. No. 9,020,580, issued Apr. 28, 2015 and titled "Systems and Methods for Monitoring Time Based Photo Active Agent Delivery or Photo Active Marker Presence," and U.S. Patent Application Publication No. 2016/0338588, filed May 23, 2016 and titled "Systems and Methods for Monitoring Cross-Linking Activity for Corneal Treatments," the contents of these applications being incorporating entirely herein by reference. In particular, U.S. Pat. No. 9,020,580 discloses an example dosimetry system that employs a modified Scheimpflug configuration. Meanwhile, U.S. Patent Application Publication No. 2016/0338588 discloses the use of hyperspectral imaging to analyze fluorescence.

Currently available cross-linking treatment systems do not indicate whether sufficient riboflavin is present in the stroma prior to initiating cross-linking treatment. This can lead to increased procedural variability and sub-optimal clinical results. Advantageously, aspects of the present disclosure address this problem by providing a quantitative, depth-resolved measurement of riboflavin concentration, which can be compared to a previously-defined target value known to provide efficacious cross-linking activity.

According to aspects of the present disclosure, embodiments specifically configure aspects of a confocal fluorescence microscope to measure riboflavin distribution in the corneal stroma as a function of depth. As such, embodiments provide an indication of whether sufficient riboflavin is present at a defined stromal depth to proceed with corneal cross-linking treatment. Embodiments may be integrated with a cross-linking treatment system as described herein or may be a standalone measurement system. Embodiments are also suitable for measuring fluorescence induced by the photoactivating UV illumination applied during the cross-linking treatment, and can thus measure the progress of cross-linking activity in real time.

According to aspects of the present invention, systems and methods can achieve one or more of the following:
1. Measure time evolution of depth profiles of riboflavin in corneal stroma at selected sites to allow cross-linking treatment to begin at more effective time(s).
2. Determine the three-dimensional (3D) distribution of riboflavin in corneal stroma as a function of time.
3. Measure depth profiles of cross-link concentration at treated sites for keeping the treatment procedure under control.
4. Reconstruct 3D distribution of cross-link concentration after treatment.
5. Locate hazy areas in corneal stroma.

To accomplish the foregoing, systems and methods may employ aspects of one or more of the following techniques:
1. Fluorescence microscopy.
2. Confocal microscopy.
3. Scheimpflug photography.
4. 3D reconstruction, image deconvolution, image registration, and other image processing techniques.

Existing confocal fluorescence microscopes require fluid immersion/contact objectives, are highly complex and expensive, and use high laser intensities, making them unsuitable for commercial use in living human corneas. Advantageously, aspects of the present disclosure address this problem by simplifying the measurement system in a manner that is optimized to provide an indication of sufficient riboflavin presence.

Figure 3:
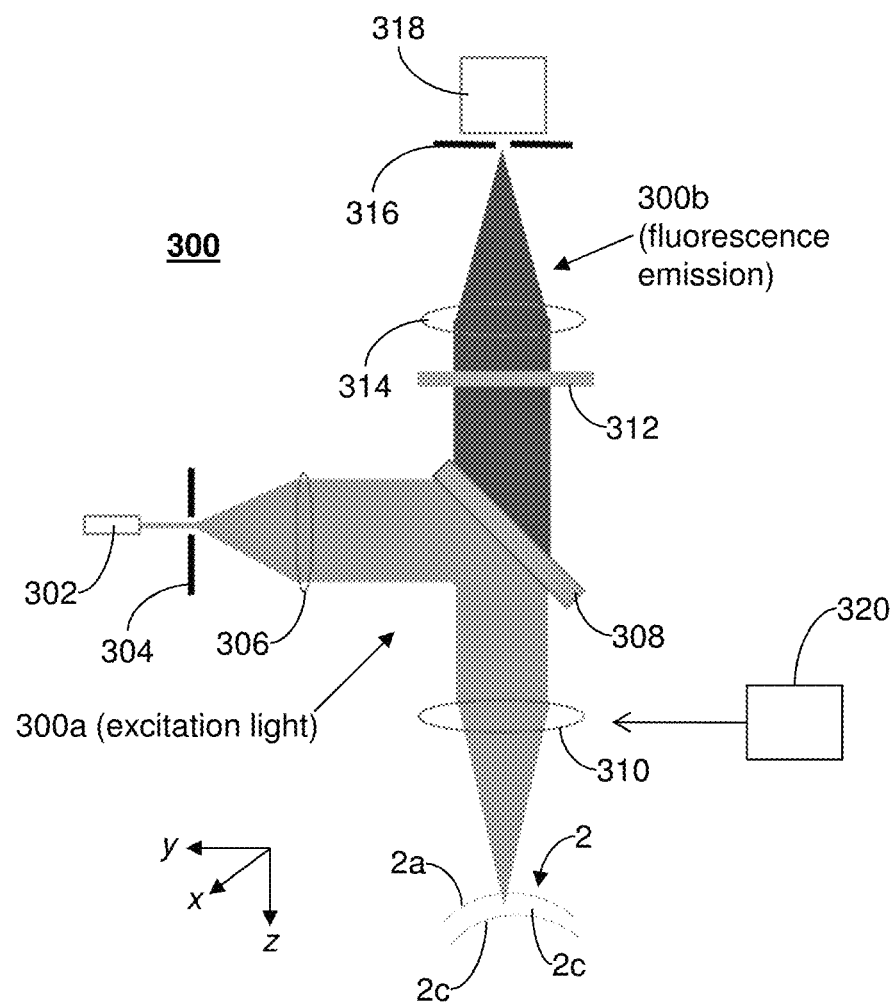
FIG. 3 illustrates an example system for measuring fluorescence associated with a distribution of a photosensitizer, e.g., riboflavin, in an eye according to aspects of the present disclosure.

To demonstrate aspects of the present disclosure, FIG. 3 illustrates an example system 300 to measure a concentration as a function of depth of exogenous cross-linking agent, e.g., riboflavin, applied to a cornea 2. The system 300 includes a laser or LED light source 302 that emits light to excite the cross-linking agent in the cornea 2. For instance, the light source 302 may emit UV excitation light, e.g., with a wavelength of 365 nm. Or the light source 302 may emit blue excitation light, e.g., with a wavelength of 458 nm, where in some cases, the light source 302 may employ a white light in combination with a blue light narrow band filter.

As shown in FIG. 3, the excitation light from the light source 302 is directed through an aperture of a light source pinhole structure 304 and a collimating lens 306. In some cases, the light source 302 may be fiber coupled. The excitation light is then directed to a dichroic filter (or mirror) 308. Due to the wavelength of the excitation light, the dichroic filter 308 reflects the excitation light toward a lens 310, such as an objective lens or similar optical element. The lens 310 focuses the excitation light to an area of the cornea 2 at a given depth along the z-axis. The transverse (x-y plane) resolution of the excitation light can be greater than 10 µm, such as approximately 10 µm to approximately 200 µm. In contrast, typical confocal microscopes require a transverse resolution of less than 10 µm.

In response to the excitation light, the cross-linking agent in the cornea 2 fluoresces. For instance, riboflavin in the cornea 2 may emit green fluorescence. The fluorescence emission travels through the lens 310 and to the dichroic filter 308. In contrast to reflecting light with the wavelength of the excitation light, the dichroic filter 308 allows the light with the fluorescence wavelength to pass to a color filter 312. The color filter 312 transmits the fluorescence emission to a lens 314, e.g., a tube lens, while blocking residual excitation light and/or other light not having a wavelength of the fluorescence emission. The lens 314 focuses the fluorescence emission to a detector 318 via an aperture of a detector pinhole 316. The detector pinhole structure 316 prevents light originating from above or below the given corneal depth from reaching the detector 318. In other words, the detector pinhole structure 316 prevents out-of-focus light from reaching the detector 318. The pinhole structure 316 may be configured to allow a lower resolution along the z-axis of greater than 10 µm, such as approximately 10 µm to approximately 100 µm. In contrast, conventional confocal microscopes require a resolution of less than 10 µm. In general, the system 300 may provide a working distance in air of greater than 10 mm and does not require fluid immersion or physical contact with the eye.

The detector 318 may be a photodiode, a photomultiplier tube, or a camera. The image plane of the detector 318 is parallel to the lens plane of the lens 314 as well as the area of excited corneal tissue along the x-y plane. This configuration allows the area of the excited corneal tissue to be uniformly in focus at the detector 318. Correspondingly, the detector pinhole structure 316 is parallel to the image plane of the detector 318.

The detector 318 is employed to quantify the amount, e.g., intensity, of fluorescence emitted from the excited area of the cornea at the given depth. The system 300 may be operated in steps to deliver excitation light to various respective depths of the cornea 2 and to detect the amount of fluorescence from the cross-linking agent at each depth. As shown in FIG. 3, the system 300 includes a scan mechanism 320 that causes the system 300 to scan the cornea 2 at various depths along the z-axis. For instance, the scan mechanism 320 may be an mechanical or electromechanical device that moves or operates the lens 310 and/or other elements of the system 300 to adjust the delivery of the excitation light to other depths. According to one implementation, the system 300 may first be operated to excite an area at the anterior surface 2a of the cornea, and then subsequently operated to excite areas at a series of depths under the anterior surface 2a to at least approximately 200 μm into the stroma 2b. The distance between two consecutive depths for delivery of the excitation light may range from approximately 10 μm to approximately 100 μm.

The amount of fluorescence detected at a given depth indicates the amount of cross-linking agent at that depth. Thus, the system 300 may be employed to confirm whether a sufficient amount of cross-linking agent is present for the start of a cross-linking treatment. Prior to proceeding with the cross-linking treatment, an amount of cross-linking agent may need to exceed a predefined threshold value at a predefined depth or set of depths.

A time series signal from the detector 318 may be sampled at a high frequency and synchronized with the scan mechanism 310 that changes the scan depth by moving one or more elements of the system 300. The information from the detector 318 may be employed to reconstruct a riboflavin concentration curve along the z-axis. For instance, the time series signal from the detector 318 can be processed to calculate: (1) the location of the posterior surface 2c of the cornea 2, (2) the riboflavin concentration as a function of depth into the cornea 2, (3) the anterior surface 2a of the cornea, (4) the distance between posterior surface 2c and the anterior surface 2a, and (5) the location of sub-corneal interfaces such as the epithelial-stroma interface.

The system 300 may include auxiliary optics, such as an imaging camera and alignment lasers, to assist in aligning the system 300 to a desired x, y, z position to initiate a scan. Additionally, several scans may be averaged together in order to increase the signal-to-noise ratio.

Furthermore, data processing algorithms may be employed to detect an incomplete scan. For instance, when a scan captures fluorescence emission from the anterior surface of the cornea 2, the information from the detector 318 indicates a sudden increase in fluorescence signal followed by a gradual decline in the fluorescence signal as the scan moves deeper from the anterior surface 2a into the stroma 2b. If the information from the detector 318 does not indicate the sudden increase in fluorescence signal, the scan likely did not capture the anterior surface 2a and may be considered incomplete.

The system 300 may provide other useful information to enhance aspects of the cross-linking treatment. For instance, the system 300 may be employed periodically or continuously to monitor the amount of fluorescence emitted by the cross-linking agent as a cross-linking treatment progresses. In particular, repeated scans over time may indicate when cross-linking activity has progressed to a desired stromal depth. Additionally, the location of the posterior surface of the cornea as detected by the system 300 can be used to align the treatment plane of the cross-linking treatment system.

In general, embodiments include an illumination path and an imaging path. The illumination path directs a point illumination to the cornea 2, and the imaging path collects fluorescence emission resulting from excitation by the point illumination. Each illumination and imaging path can use an on-axis or an off-axis configuration. The system 300 shown in FIG. 3 is an on-axis optical system. The system 300 employs an on-axis illumination path 300a, where the area of excited corneal tissue along the x-y plane is perpendicular to the illumination path 300a for the excitation light. The system 300 also employs an on-axis imaging path 300b, where the area of excited corneal tissue along the x-y plane is perpendicular to the imaging path for the fluorescence emission.

In embodiments where both the illumination path and the imaging path are on-axis, the illumination path and imaging path can be on either reflective side or transmission side of the dichroic mirror. As shown in FIG. 3, for instance, the illumination path 300a is on the reflective side of the dichroic filter 308, while the imaging path 300b is on the transmission side of the dichroic filter 308. In particular, the excitation light from the light source 302 is directed to the dichroic filter 308, which reflects the excitation light, e.g., 90°, toward the cornea 2 based on the wavelength of the excitation light. The dichroic filter 308 allows the fluorescence emission to pass toward the detector 318 based on the wavelength of the fluorescence emission.

Figure 4:
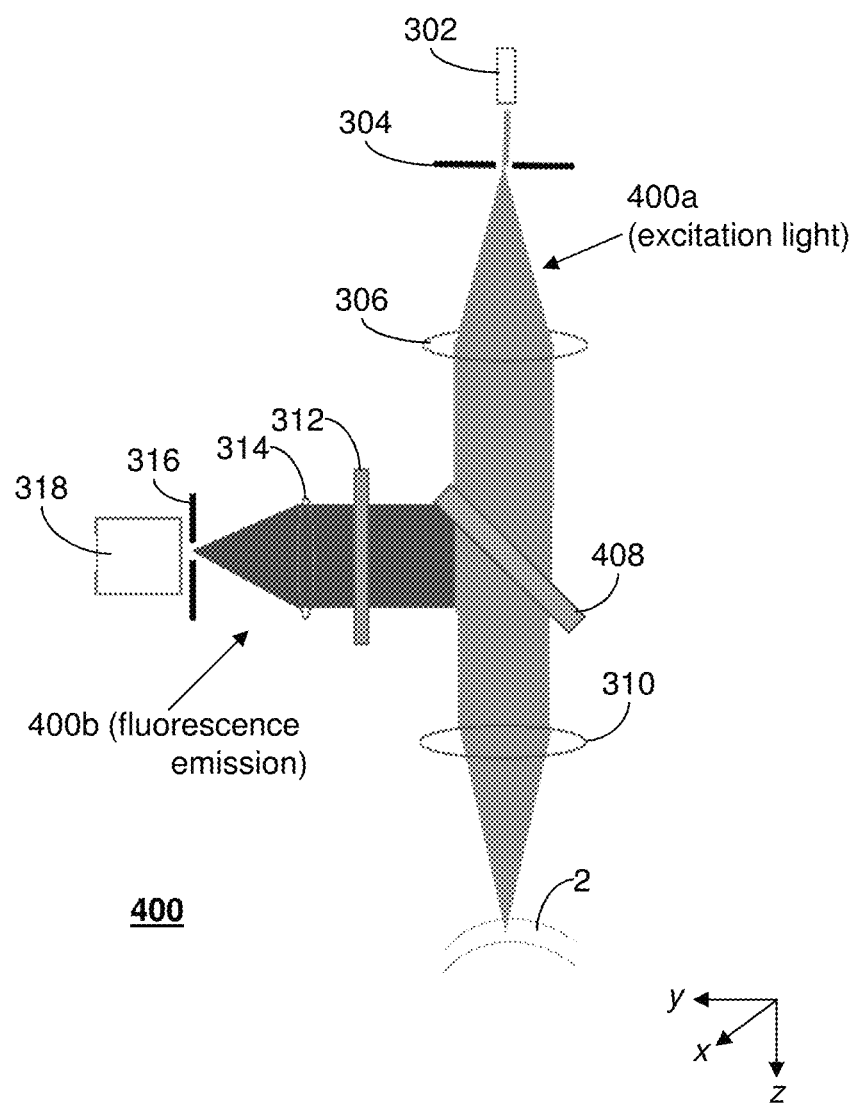
FIG. 4 illustrates another example system for measuring fluorescence associated with a distribution of a photosensitizer, e.g., riboflavin, in an eye according to aspects of the present disclosure.

On the other hand, FIG. 4 illustrates an example system 400, which is similar to the system 300, but includes an illumination path 400a disposed on the transmission side of a dichroic mirror 408 and an imaging path 400b disposed on the reflective side of the dichroic mirror 408. In particular, the excitation light from the light source 302 is directed to the dichroic filter 408, which allows the excitation light to pass toward the cornea 2 based on the wavelength of the excitation light. Meanwhile, the dichroic filter 408 reflects the fluorescence emission, e.g., 90°, toward the detector 318 based on the wavelength of the fluorescence emission.

Figure 5:
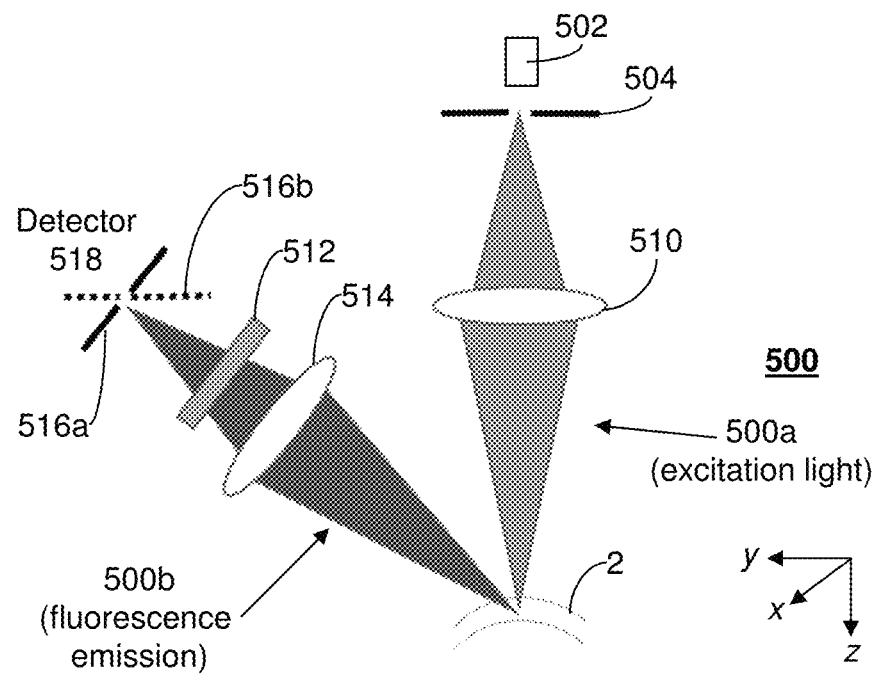
FIG. 5 illustrates yet another example system for measuring fluorescence associated with a distribution of a photosensitizer, e.g., riboflavin, in an eye according to aspects of the present disclosure.

In contrast to the example systems 300, 400 above, FIG. 5 illustrates an example system 500 employing an on-axis illumination path 500a and an off-axis imaging path 500b. A light source 502 emits light to excite the cross-linking agent in the cornea 2. The excitation light from the light source 502 is directed through an aperture of a light source pinhole structure 504 and to a lens 510, such as an objective lens or similar optical element. The lens 510 focuses the excitation light to an area of the cornea 2 along the x-y plane at a given depth along the z-axis. As shown in FIG. 5, the area of excited corneal tissue along the x-y plane is perpendicular to the illumination path 500a for the excitation light. As such, the illumination path 500b is considered to be on-axis.

In response to the excitation light, the cross-linking agent in the cornea 2 fluoresces. The fluorescence emission travels through a lens 514 and a color filter 512. The lens 514 focuses the fluorescence emission onto a detector 518. The color filter 512 blocks residual excitation light and/or other light not having a wavelength of the fluorescence emission.

The fluorescence emission passes through an aperture of a detector pinhole structure 516a (solid line) or alternatively 516b (dashed line), which prevents light originating from above or below the given corneal depth from reaching the detector 518. The detector 518 may be a photodiode, a photomultiplier tube, or a camera. The detector 518 may be employed to quantify the amount, e.g., intensity, of fluorescence emitted from the excited area of the cornea at the given depth.

The area of excited corneal tissue along the x-y plane is not perpendicular to the imaging path 500b for the fluorescence emission. In other words, the imaging path 500b extends from the x-y plane at the given depth at an angle that is not equal to 90°. As such, the imaging path 500b is considered to be off-axis.

According to one embodiment, the image plane of the detector 518 is parallel to the lens plane of the lens 514. As shown in FIG. 4, the detector pinhole structure 516a is correspondingly parallel to the image plane and the lens plane, i.e., perpendicular to the imaging path 500b.

According to an alternative embodiment, the image plane of the detector 518 is not parallel to the lens plane of the lens 514. Instead, the detector 518 and the lens 514 are arranged so that the image plane and the lens plane are in a Scheimpflug configuration. In this configuration, the excited area of corneal tissue along the x-y plane is more uniformly in focus at the detector 518, even though the imaging path 500b is not perpendicular to the excited area of corneal tissue. The detector pinhole structure 516b is correspondingly angled relative to the image plane and the lens plane, e.g., parallel to the x-y plane, to prevent light originating from above or below the given corneal depth from reaching the detector 518.

Figure 6:
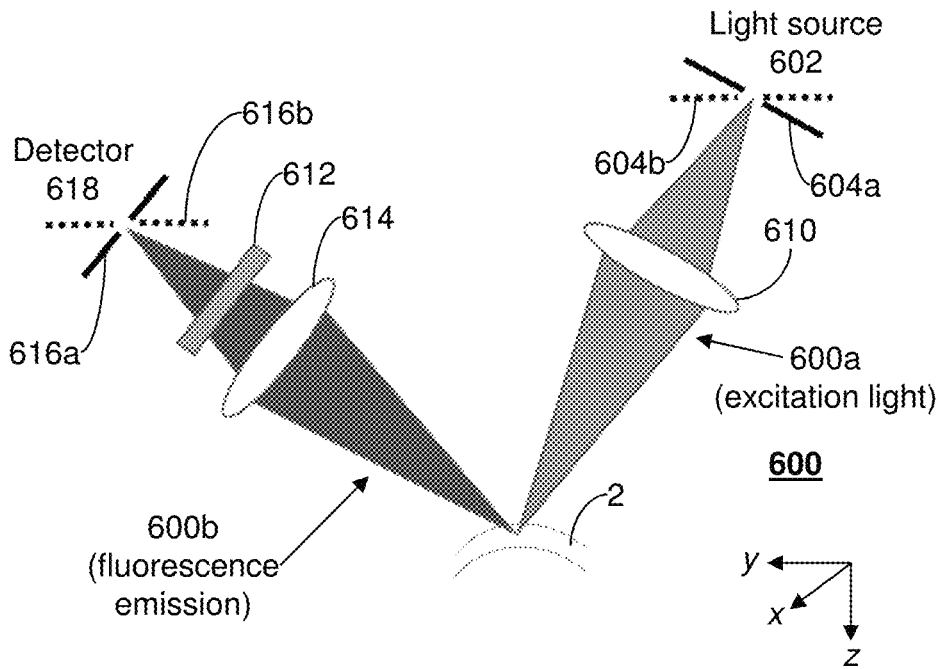
FIG. 6 illustrates a further example system for measuring fluorescence associated with a distribution of a photosensitizer, e.g., riboflavin, in an eye according to aspects of the present disclosure.

FIG. 6 illustrates an example system 600 employing an off-axis illumination path 600a and an off-axis imaging path 600b. A light source 602 emits a light to excite the cross-linking agent in the cornea 2. The excitation light from the light source 602 is directed through an aperture of a light source pinhole structure 604a (solid line) or alternatively 604b (dashed line), and then to a lens 610, such as an objective lens or similar optical element. The lens 610 focuses the excitation light to an area of the cornea 2 along the x-y plane at a given depth along the z-axis.

The area of excited corneal tissue along the x-y plane is not perpendicular to the illumination path 600a for the excitation light. In other words, the illumination path 600a extends to the x-y plane at the given depth at an angle that is not equal to 90°. As such, the illumination path 600a is considered to be off-axis.

In response to the excitation light, the cross-linking agent in the cornea 2 fluoresces. The fluorescence emission travels through a lens 614 and a color filter 612. The lens 614 focuses the fluorescence emission onto a detector 618. The color filter 612 blocks residual excitation light and/or other light not having a wavelength of the fluorescence emission. The fluorescence emission passes through an aperture of a detector pinhole structure 616a (solid line) or 616b (dashed line), which prevents light originating from above or below the given corneal depth from reaching the detector 618. The detector 618 may be a photodiode, a photomultiplier tube, or a camera. The detector 618 may be employed to quantify the amount, e.g., intensity, of fluorescence emitted from the excited area of the cornea at the given depth.

The area of excited corneal tissue along the x-y plane is not perpendicular to the imaging path 600b for the fluorescence emission. In other words, the imaging path 600b extends from the x-y plane at the given depth at an angle that is not equal to 90°. As such, the imaging path 600b is considered to be off-axis.

According to one embodiment, the image plane of the detector 618 is parallel to the lens plane of the lens 614. As shown in FIG. 6, the detector pinhole structure 616a is also parallel to the image plane and the lens plane and perpendicular to the imaging path 600b. Correspondingly, the light source pinhole structure 604a is also perpendicular to the illumination path 600a.

According to an alternative embodiment, the image plane of the detector 618 is not parallel to the lens plane of the lens 614. Instead, the detector 618 and the lens 614 are arranged so that the image plane and the lens plane are in a Scheimpflug configuration. In this configuration, the excited area of corneal tissue along the x-y plane is more uniformly in focus at the detector 618, even though the imaging path 600b is not perpendicular to the excited area of corneal tissue. The detector pinhole structure 616b is angled relative to the image plane and the lens plane and not perpendicular to the imaging path 600b. Correspondingly, the light source 602 and the lens 610 are arranged so that the light source plane and the lens plane are in a Scheimpflug configuration. Additionally, the light source pinhole structure 604b is angled relative to the light source plane and the lens plane and not perpendicular to the illumination path 600a. In this configuration, the excitation light is focused more uniformly to the excited area of corneal tissue along the x-y plane. The light source pinhole structure 604b and the detector pinhole structure 616b may be parallel to the x-y plane.

The example systems described above may employ pinhole apertures to create a single point illumination; however, a pinhole array or slit illumination may be alternatively employed. In cases where an example system is incorporated into a cross-linking treatment system as described above, slit illumination can be generated via a DMD. Although slit illumination may be employed for illumination, a pinhole aperture or perpendicular slit in the imaging path may be sufficient to collect the fluorescence emission.

In cases where the illumination path employs a Scheimpflug configuration, as shown for instance in FIG. 6, a dots array may be generated using masks, gratings, acoustic optics, diffraction optical element (DOE), etc. The dots array is aligned along the z-axis and has separation larger than the axial resolution of the imaging path.

In the example systems 500, 600, the fluorescence emission is collected from a smaller corneal region defined by an overlap between the illumination and imaging paths. As such, a smaller volume of corneal tissue can be interrogated by the systems 500, 600. Advantageously, this may allow the optical requirements or constraints on the pinhole structures and numerical apertures of the respective lenses to be relaxed, which may in turn allow a larger working distance between the systems 500, 600 and the subject.

Relative motion between the eye and the example system 300, 400, 500, or 600, i.e., scanning, allows the system to generate and measure fluorescence emission at different depths along the z-axis. The example systems might scan only along the z-axis and not along the x- and y-axes. Scanning along the z-axis can be achieved according to various approaches. According to one approach, aspects of a system can be actively moved along the z-axis while the subject's eye remains at a fixed position x, y, z. The entire system or certain components can be moved along the z-axis by a motor or the like.

According to another approach, a system can scan along the z-axis by actively moving the subject's eye at a high frequency. In this approach, the subject's head may be situated in a chair that can be moved up and down along the z-axis for a small range at high frequency while the system remains at a fixed position x, y, z.

Figure 7:
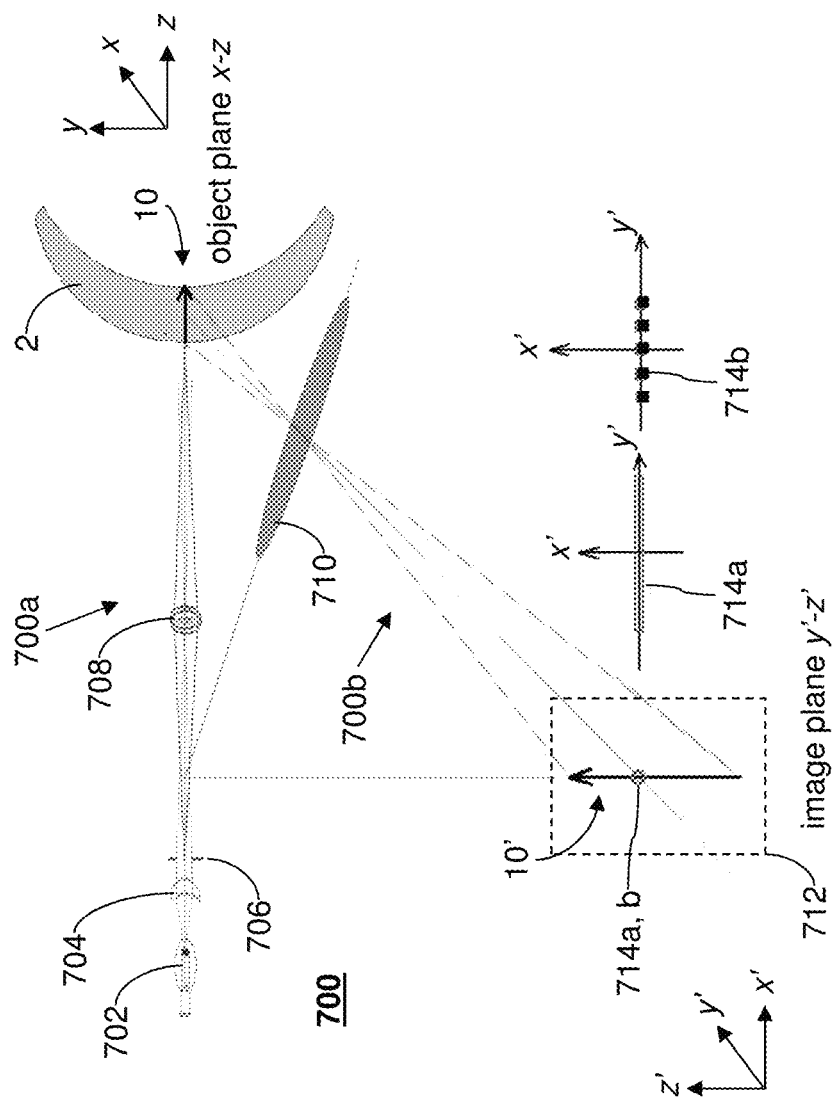
FIG. 7 illustrates yet a further example system for measuring fluorescence associated with a distribution of a photosensitizer, e.g., riboflavin, in an eye according to aspects of the present disclosure.

To demonstrate further aspects of the present disclosure, FIG. 7 illustrates an example system 700 for detecting fluorescence associated with a distribution of a cross-linking agent, e.g., riboflavin, in a cornea 2. The system 700 includes an illumination path 700a that projects a slit light pattern 10 into tissue, e.g., stroma, of the cornea 2 via a slit lamp. For instance, to generate the light pattern 10, the system may employ a light source 702 that directs an excitation light to at least a collector lens 704, a slit 706, and an objective lens 708, which are configured according to the principles of Kohler illumination. As shown in FIG. 7, the light source 702 may include a filament, and with the Kohler configuration, the filament is imaged on the objective lens 708 while the slit 706 is imaged at the cornea 2.

The x-, y-, z-axes shown in FIG. 7 define an object space corresponding to the light pattern 10 received by the cornea 2. The light pattern 10 extends from anterior to posterior along the x-z plane. The cross-linking agent exposed to the light pattern 10 in the cornea 2 is excited and emits fluorescence. The system 700 includes an imaging path 700b, which includes at least a Scheimpflug lens 710. The Scheimpflug lens 710 transmits the fluorescence emission to a detector 712. A magnified image 10' of the pattern 10 is created at the image plane of the detector 712. The x'-, y'-, z'-axes shown in FIG. 7 define an image space corresponding to the image 10'. A bandpass filter may be employed in the imaging path to attenuate the excitation light and other stray light.

In one embodiment, the system 700 employs a long movable slit aperture 714a in the image plane that can scan along the z'-axis. The aperture 714a is scanned over an array of pixels, e.g., a CCD array, corresponding to the fluorescence emission. Scanning the aperture along the z'-axis over a proper range yields the fluorescence intensity profile in the cornea 2. This profile is recorded for the z-direction (direction of corneal depth) in the object space and is averaged in the x-direction over the slit length (mapped to the object space).

The example system 700 provides fast acquisition of the depth profiles due to a relatively large aperture size. The profiles, however, are unresolved in the lateral direction, i.e., along the x-axis. If a certain spatial resolution in the lateral direction is desired, alternative embodiments may employ a lenticular array of pinhole apertures 714b rather than the slit aperture 714a. A single scan of the pinhole aperture array 714b along the z'-axis yields a two-dimensional profile of fluorescence intensity spatially resolved in both the z-direction (direction of corneal depth) and the x-direction (lateral direction). The aperture size (width of slit aperture, pinhole aperture diameter) may be selected to balance acquisition rate and spatial resolution.

Figure 8:
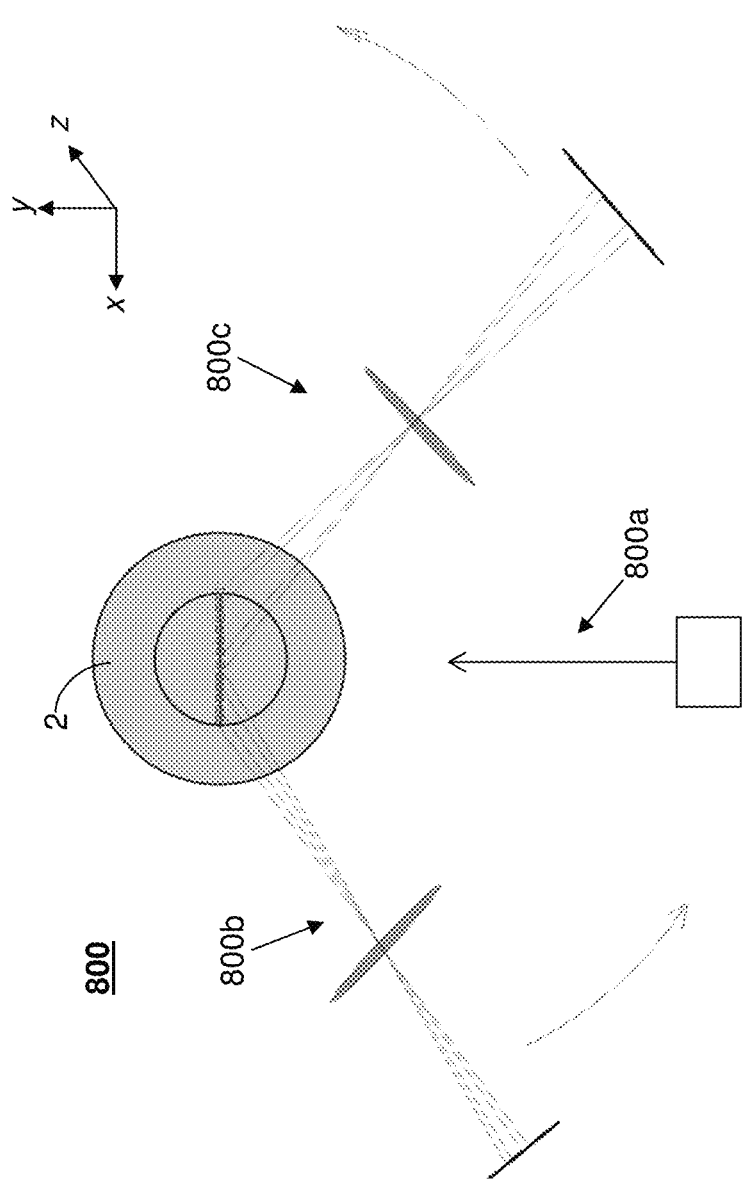
FIG. 8 illustrates an additional example system for measuring fluorescence associated with a distribution of a photosensitizer, e.g., riboflavin, in an eye according to aspects of the present disclosure.

FIG. 8 illustrates aspects of another example system 800 that acquires a three-dimensional profile of the fluorescence emission due to the response to excitation light of a cross-linking agent in the cornea 2. The system 800 includes an illumination path 800a for providing the excitation light. The illumination path 800a, for instance, may be generated according to any of the embodiments described above. To capture the fluorescence emission, the system 800 includes a first imaging path 800b and a second imaging path 800c. The system 800 rotates the illumination path 800a and the first and second imaging paths 800b, c around the eye by 180° to yield a dataset of images, which provide the three-dimensional profile. The three-dimensional profile indicates the presence of cross-linking agent in a volume of corneal tissue. The may involve several steps, e.g.:

1. Deconvolution—removing the blurring effect related to the finite aperture size.
2. Correction for variable magnification of Scheimpflug lens over the field of view.
3. Refraction correction—removing the image distortion due to the refraction of light at the anterior corneal surface.
4. Smoothing—removing high spatial frequency components of the image due to shot noise (small number of photons per pixel) and diffractive patterns.
5. Corrections for eye movements during the recording time of the image.

A proper calibration procedure may be developed for the image distortion correction.

According to aspects of the present invention, embodiments may include a two-channel design including illumination and detection channels, as shown for example in FIG. 7.

Embodiments may include an illumination channel providing a collimated slit or pixel beam in the corneal stroma, as shown for example in FIG. 7.

Embodiments may include an eye-tracking channel.

Embodiments may include an illumination channel that is a part of eye tracking optics (e.g., tracking of corneal apex with Purkinje images).

Embodiments may include an illumination channel that may include one of the following: a commercial or OEM slit lamp, or pixel projection optics.

Embodiments may include an illumination beam that acts as a source of stray light propagating in different directions. Physical mechanisms of the stray light generation may include riboflavin fluorescence, cross-Link fluorescence and/or bulk scattering of stromal tissue.

Embodiments may include a detection channel that picks up the stray light transferring the light rays to image plane through a high numerical aperture (NA) lens, as shown for example in FIG. 7. The object plane of the lens (conjugate to the image plane) is aligned to the illumination beam in stroma using the Scheimpflug principle, as shown for example in FIG. 7. Using the Scheimpflug principle makes it possible to image the illuminated slit or other pattern between the anterior and posterior corneal surfaces at a convenient angle, e.g., 45°, as shown for example in FIG. 7.

The thickness of the optical slice contributing to the image may be significantly reduced by using high NA lens and confocal principal. The latter principle means that a small aperture is scanned over the image plane while the image is recorded. In some embodiments, a CCD array may be used where the pixels are switched on in certain order until the whole area is covered. The pixel switching order must be chosen to minimize their cross-talk (either electrical or optical).

According to further aspects of the present disclosure, embodiments may be employed to provide a high-resolution, non-contact pachymeter. As described above, embodiments can quantify the amount, e.g., intensity, of fluorescence emitted by a cross-linking agent in the cornea at various depths in response to an excitation light. For instance, as shown in FIG. 3, the system 300 can scan the cornea 2 at various depths along the z-axis to measure concentration of cross-linking agent as a function of corneal depth. Such a scan may be sufficient to assess the entire thickness of the cornea. In particular, the scan may extend from at least the interface between external air and the cornea (i.e., anterior surface of the cornea) to the interface between the endothelium and the anterior chamber (i.e., posterior surface of the cornea). As also described above, when a detector of an embodiment captures fluorescence emission from the anterior surface of the cornea, there is a sudden increase in fluorescence signal followed by a gradual decline in the fluorescence signal as the scan moves deeper from the anterior surface into the stroma. When the scan reaches the interface between the endothelium and the anterior chamber (posterior surface), the fluorescence signal suddenly decreases to zero. By measuring the distance between the depths at which the sudden increase (signal peak) and the sudden decrease (to zero) in fluorescence signal are detected, the corneal thickness can be determined. Thus, in addition to providing information on the presence of a cross-linking agent in the cornea, embodiments can provide a measurement of corneal thickness. A measurement of corneal thickness is typically required prior to a cross-linking treatment to ensure safety of the endothelium.

To reduce measurement noise and to obtain a more accurate measurement of corneal thickness, multiple scans extending through the thickness of the cornea (e.g., along the z-axis as shown in FIG. 3) may be conducted at different transverse positions across the cornea (e.g., at different (x, y) positions as shown in FIG. 3). The measurements from these multiple scans can then be averaged. A pachymetry map covering a predefined or user-selected set of transverse positions may be generated to assess, for instance, central corneal thickness and/or peripheral corneal thickness. For instance, a pachymetry map may be generated over a section associated with a keratoconic defect.

Using aspects of confocal fluorescence microscopy, embodiments can achieve high resolution (e.g., less than 100 µm) and rapid (e.g., less than one second) measurement of corneal thickness. Additionally, such measurement can be taken without physically contacting the cornea, thereby enhancing safety and comfort for the subject. Furthermore, this approach to pachymetry is insensitive to variations in density, hydration state, and refractive properties of the cornea. Also, this approach is insensitive to the presence of haze sometimes associated with eyes, especially with diseased eyes. As such, this approach can provide more accurate measurements of corneal thickness in contrast, for instance, with ultrasound-based approaches, which rely on a single nominal speed of sound to measure corneal thickness.

Rather than detecting signals based on fluorescence emission from a cross-linking agent in a cornea in response to excitation light, alternative implementations of the embodiments above can determine corneal thickness by detecting signals based on incidence light that is reflected from a cornea, where no cross-linking agent is present in the cornea. The reflected light from a scan through the cornea provides signals that indicate the presence of the anterior surface of the cornea and the posterior surface of the cornea. In particular, signal spikes or other signal changes may mark the anterior and posterior surfaces of the cornea. Advantageously, this alternative implementation can provide reliable measurements of corneal thickness independent of any presence of cross-linking agent in the cornea.

Figure 9:
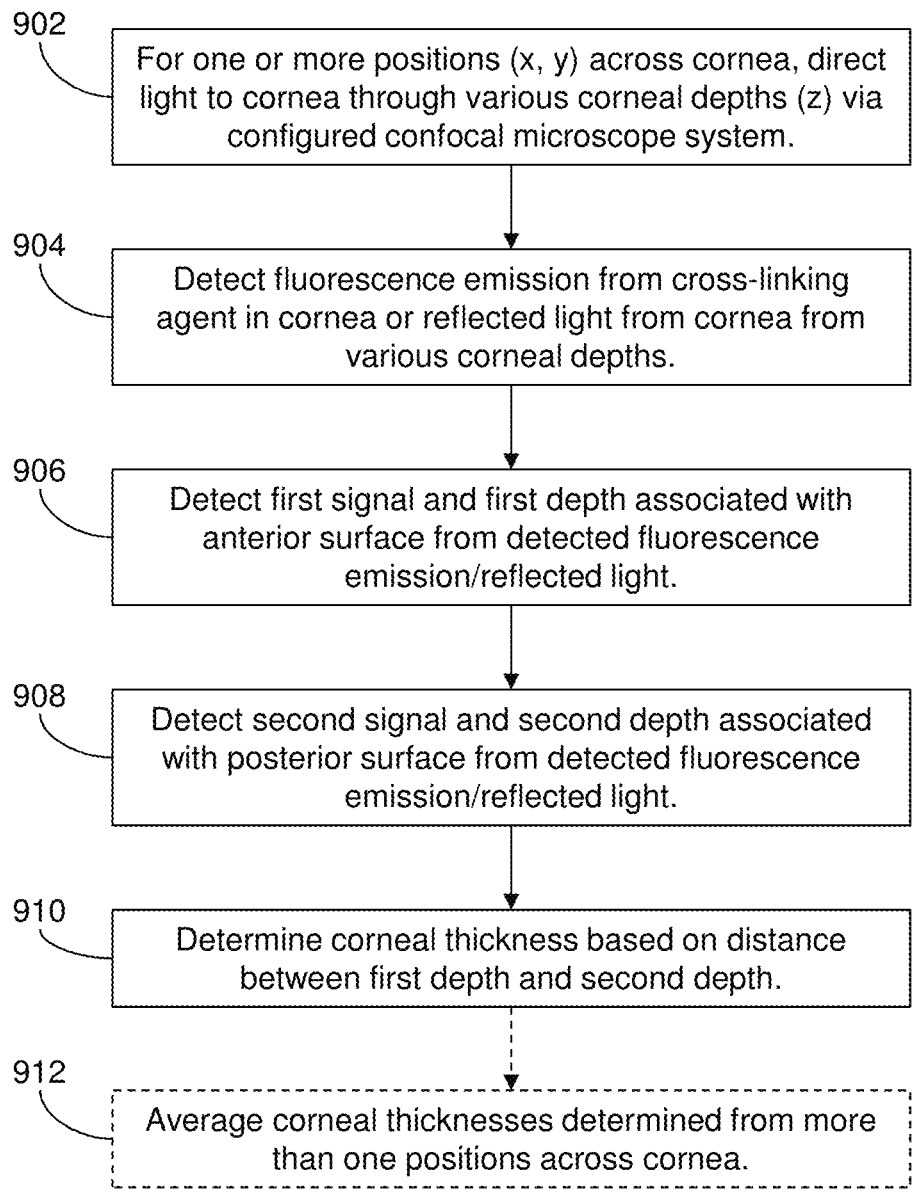
FIG. 9 illustrates an example approach for measuring corneal thickness according to aspects of the present disclosure.

In summary, FIG. 9 generally illustrates an example approach 900 for measuring corneal thickness via embodiments that employ aspects of confocal microscopy. In act 902, for one or more positions (x, y) across a cornea, light is directed to the cornea through various corneal depths (z) via a configured confocal microscope system. In act 904, fluorescence emission from a cross-linking agent in the cornea or reflected light from the cornea without a cross-linking agent is detected from the various corneal depths. In act 906, a first signal and a corresponding first depth associated with the anterior surface of the cornea is detected from the fluorescence emission/reflected light. In act 908, a second signal and a corresponding second depth associated with the posterior surface of the cornea is detected from the fluorescence emission/reflected light. In act 910, a corneal thickness is determined from a distance between the first depth and the second depth. In optional act 912, if there is more than one position (x, y) across the cornea, the corneal thicknesses from the more than one positions are averaged to determine a more accurate measurement.

As described above, according to some aspects of the present disclosure, some or all of the steps of the above-described and illustrated procedures can be automated or guided under the control of a controller (e.g., the controller 120). Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the example embodiments of the present disclosure, as is appreciated by those skilled in the computer and software arts. The physical processors and/or machines may be externally networked with the image capture device(s), or may be integrated to reside within the image capture device. Appropriate software can be readily prepared by programmers of ordinary skill based on the teachings of the example embodiments, as is appreciated by those skilled in the software art. In addition, the devices and subsystems of the example embodiments can be implemented by the preparation of application-specific integrated circuits or by interconnecting an appropriate network of conventional component circuits, as is appreciated by those skilled in the electrical art(s). Thus, the example embodiments are not limited to any specific combination of hardware circuitry and/or software.

Stored on any one or on a combination of computer readable media, the example embodiments of the present disclosure may include software for controlling the devices and subsystems of the example embodiments, for driving the devices and subsystems of the example embodiments, for enabling the devices and subsystems of the example embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the example embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the example embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the present disclosure. It is also contemplated that additional embodiments according to aspects of the present disclosure may combine any number of features from any of the embodiments described herein.

What is claimed is:

1. A measurement system for a cornea, comprising:
   a light source configured to emit light;
   at least one optical element positioned to receive the light from the light source and configured to focus the light to an area of corneal tissue at a selected depth of the cornea, a light signal being generated at the area of corneal tissue in response to the light from the light source;
   a pinhole structure including an aperture, the pinhole structure positioned to receive the light signal generated at the area of corneal tissue, the aperture being configured to selectively transmit the light signal from the area of corneal tissue at the selected depth;
   a detector positioned to capture the light signal transmitted by the aperture and configured to communicate information relating to a measurement of the light signal captured by the detector, wherein the pinhole structure prevents light above or below the selected depth from reaching the detector; and
   a controller communicatively coupled to the detector and configured to receive the information from the detector and to determine, based on the information, a measurement of the light signal generated at the area of corneal tissue at the selected depth.

2. The measurement system of claim 1, wherein the light signal is a fluorescence emission from the area of corneal tissue.

3. The measurement system of claim 1, wherein the light signal is reflected light from the area of corneal tissue.

4. The measurement system of claim 1, wherein the measurement of the light signal generated at the area of corneal tissue indicates a measurement of cross-linking activity at the selected depth.

5. The measurement system of claim 1, wherein the measurement of the light signal is determined according to a resolution of greater than 10 μm along an axis corresponding to the depth of the corneal tissue and/or a plane transverse to the axis.

6. The measurement system of claim 1, further comprising a scan mechanism configured to cause the at least one optical element to scan the cornea at a plurality of depths and to focus the light from the light source on a respective area of corneal tissue at each depth,
   wherein for each depth:
   (i) the aperture of the pinhole structure is configured to selectively transmit the light signal from the respective area of corneal tissue, and
   (ii) the detector is configured to capture the light signal transmitted by the aperture and to communicate information relating to a measurement of the light signal captured by the detector, and
   the controller is configured to receive the information from the detector for each depth and to determine, based on the information for the plurality of depths, a measurement of the light signal in the cornea as a function of depth.

7. The measurement system of claim 6, wherein the scan mechanism is configured to cause the at least one optical element to scan, more than one time, the cornea at the plurality of depths, and the controller is further configured to determine, based on the information from the more than one scans, an amount of cross-linking activity as a function of time and depth.

8. The measurement system of claim 6, wherein the plurality of depths extend from an anterior surface of the cornea to at least approximately 200 μm into the cornea, and adjacent depths in the plurality of depths are separated by approximately 10 μm to approximately 100 μm.

9. The measurement system of claim 1, further comprising a scan mechanism configured to cause the at least one optical element to scan the cornea at a plurality of transverse locations across each of a plurality of depths and to focus the light from the light source on a respective area of corneal tissue at each transverse location at each depth,
   wherein for each transverse location at each depth:
   (i) the aperture of the pinhole structure is configured to selectively transmit the light signal from the respective area of corneal tissue, and
   (ii) the detector is configured to capture the light signal transmitted by the aperture and to communicate information relating to a measurement of the light signal captured by the detector, and the controller is configured to receive the information from the detector for each transverse location and to determine, based on the information for the plurality of the transverse locations at the plurality of depths, a measurement of the light signal in the cornea as a function of transverse location and depth.

10. The measurement system of claim 9, wherein the scan mechanism is configured to cause the at least one optical element to scan, more than one time, the cornea at the plurality of depths and the plurality of transverse locations, and the controller is further configured to determine, based on the information from the more than one scans, an amount of cross-linking activity as a function of time, depth, and transverse location.

11. A method for monitoring a cornea, comprising:
    emitting light from a light source;
    receiving, by at least one optical element, the light from the light source;
    focusing, by the at least one optical element, the light from the light source to an area of corneal tissue at a selected depth of the cornea;

receiving, by a pinhole structure, a light signal generated at the area of corneal tissue at the selected depth in response to the light from the light source;

selectively transmitting, by an aperture of the pinhole structure, the light signal generated at the area of corneal tissue at the selected depth;

capturing, by a detector, the light signal transmitted by the aperture, wherein the pinhole structure prevents light above or below the selected depth from reaching the detector;

communicating to a controller, by the detector, information relating to a measurement of the light signal captured by the detector;

determining, by the controller, a measurement of the light signal generated at the area of corneal tissue at the selected depth based on the information from the detector.

12. The method of claim 11, wherein the light signal is a fluorescence emission from the area of corneal tissue.

13. The method of claim 11, wherein the light signal is reflected light from the area of corneal tissue.

14. The method of claim 11, wherein the measurement of the light signal generated at the area of corneal tissue indicates a measurement of cross-linking activity at the selected depth.

15. The method of claim 11, wherein the measurement of the light signal is determined according to a resolution of greater than 10 μm along an axis corresponding to the depth of the corneal tissue and/or a plane transverse to the axis.

16. The method of claim 11, further comprising:
scanning, with the at least one optical element, the cornea at a plurality of depths, wherein the light from the light source is focused on a respective area of corneal tissue at each depth,
wherein for each depth:
(i) the aperture of the pinhole structure selectively transmits the light signal from the respective area of corneal tissue, and
(ii) the detector captures the light signal transmitted by the aperture and communicates information relating to a measurement of the light signal captured by the detector, and
the controller receives the information from the detector for each depth and determines, based on the information for the plurality of depths, a measurement of the light signal in the cornea as a function of depth.

17. The method of claim 16, wherein the at least one optical element scans, more than one time, the cornea at the plurality of depths, and the controller further determines, based on the measurement of the light signal in the cornea as a function of depth for each scan, an amount of cross-linking activity as a function of time and depth.

18. The method of claim 16, wherein the plurality of depths extend from an anterior surface of the cornea to at least approximately 200 μm into the cornea, and adjacent depths in the plurality of depths are separated by approximately 10 μm to approximately 100 μm.

19. The method system of claim 16, further comprising:
scanning, with the at least one optical element, the cornea at a plurality of transverse locations across each of a plurality of depths, wherein the light from the light source is focused on a respective area of corneal tissue at each transverse location at each depth,
wherein for each transverse location at each depth:
(i) the aperture of the pinhole structure is configured to selectively transmit the light signal from the respective area of corneal tissue, and
(ii) the detector is configured to capture the light signal transmitted by the aperture and to communicate information relating to a measurement of the light signal captured by the detector, and the controller is configured to receive the information from the detector for each transverse location and to determine, based on the information for the plurality of the transverse locations at the plurality of depths, a measurement of the light signal in the cornea as a function of transverse location and depth.

20. The method of claim 19, wherein the at least one optical element scans, more than one time, the cornea at the plurality of depths and the plurality of transverse locations, and the controller further determines, based on the measurement of the light signal in the cornea as a function of transverse location and depth for each scan, an amount of cross-linking activity as a function of time, depth, and transverse location.

* * * * *